(12) United States Patent
Tamura

(10) Patent No.: US 7,173,269 B2
(45) Date of Patent: Feb. 6, 2007

(54) APPARATUS FOR PROCESSING PHOTOSENSITIVE MATERIAL AND AREA MEASUREMENT METHOD

(75) Inventor: Naoki Tamura, Kyoto (JP)

(73) Assignee: Dainippon Screen Mfg. Co., Ltd., Kyoto (JP)

( * ) Notice: Subject to any disclaimer, the term of this patent is extended or adjusted under 35 U.S.C. 154(b) by 0 days.

(21) Appl. No.: 11/196,324

(22) Filed: Aug. 4, 2005

(65) Prior Publication Data

US 2006/0043321 A1    Mar. 2, 2006

(30) Foreign Application Priority Data

Aug. 30, 2004   (JP)   ............... 2004-249391

(51) Int. Cl.
*G01N 21/86* (2006.01)

(52) U.S. Cl. ............... 250/559.24; 250/559.36; 356/637; 396/568

(58) Field of Classification Search ........... 250/559.19, 250/559.22, 559.24, 559.29, 559.36; 396/567–569; 356/628, 635, 637; 399/370, 376
See application file for complete search history.

(56) References Cited

U.S. PATENT DOCUMENTS 6,672,778 B2    1/2004   Sato et al.
2003/0072574 A1*  4/2003   Sato et al. ............... 396/564

FOREIGN PATENT DOCUMENTS

JP    04-163555   *   6/1992
JP    2001-100432       4/2001

* cited by examiner

*Primary Examiner*—Thanh X. Luu
(74) *Attorney, Agent, or Firm*—McDermott Will & Emery LLP

(57) ABSTRACT

A plurality of microswitches are arranged in a photosensitive material receiving section in a row, in a direction perpendicular to the travel direction of a printing plate. The printing plate is carried while being centered with respect to a center of a transport path. The plurality of microswitches are arranged in an asymmetrical manner with respect to the center of the transport path. Thus the width of a photosensitive material can be precisely calculated with a small number of microswitches. Further, deviation of the photosensitive material from the center of the transport path can be easily detected.

13 Claims, 5 Drawing Sheets

PRIOR ART

APPARATUS FOR PROCESSING PHOTOSENSITIVE MATERIAL AND AREA MEASUREMENT METHOD

BACKGROUND OF THE INVENTION

1. Field of the Invention

The present invention relates to an apparatus for processing a photosensitive material in which a photosensitive material such as a printing plate is processed using a processing liquid such as a developer. The present invention also relates to an area measurement method for measuring the area of a photosensitive material.

2. Description of the Background Art

An apparatus for processing a photosensitive material has been in practical use in which a photosensitive material is processed while being carried along a predetermined transport path. As an example, a dip-type apparatus for processing a photosensitive material is publicly known that processes a photosensitive material dipped in a processing tank storing a processing liquid. Such a dip-type processing apparatus is provided with a replenishment mechanism that adds a replenisher to a processing liquid in the processing tank in response to the process upon the photosensitive material. The addition of the replenisher is intended to compensate for the reduction of the degree of activity of the processing liquid.

In some cases, the replenishment mechanism measures the area of the photosensitive material and then adds the replenisher in an amount responsive to the measured area. The replenishment mechanism operating in this manner has a plurality of photosensitive material detectors for measuring the area of the photosensitive material arranged across the width of the photosensitive material. As an example, the photosensitive material detectors are photoelectric sensors or mechanical microswitches provided near the entrance of the processing apparatus. The photosensitive material detectors each detect the presence or absence of the photosensitive material directly thereover or thereunder.

FIG. 5 shows the arrangement of photosensitive material detectors in a conventional apparatus for processing a photosensitive material. A photosensitive material is carried in a direction indicated by an arrow A in FIG. 5. A plurality of photosensitive material detectors are arranged in a row in a direction B perpendicular to the direction A, in a symmetrical manner about a line L as the center line of the width of a transport path of a photosensitive material. Photosensitive material detectors arranged on one of sides with respect to the center line L (the right-hand side of FIG. 5) are identified as 114a, 114b, 114c and 114d in this order when viewed from the center line L. Photosensitive material detectors arranged on the other side (the left-hand side of FIG. 5) are identified as 114a', 114b', 114c' and 114d' in this order when viewed from the center line L.

A photosensitive material with every width is carried, with its center of the width coinciding with the center line L of the transport path. Thus in this processing apparatus, four different widths of a photosensitive material can be identified. More specifically, of a first range of less than a distance d1 between the photosensitive material detectors 144a and 144a', a second range of not less than the distance d1 and less than a distance d2 between the photosensitive material detectors 144b and 144b', a third range of not less than the distance d2 and less than a distance d3 between the photosensitive material detectors 144c and 144c', and a fourth range of not less than the distance d3 and less than a distance d4 between the photosensitive material detectors 144d and 144d', it is determined which of the first, second, third and fourth ranges the width of a photosensitive material has.

In order to improve timing accuracy in adding a replenisher to a processing liquid in a processing tank, the width of a photosensitive material is desirably measured at increased resolution. This may be realized by the less space between photosensitive material detectors. However, due to restriction imposed by the size of photosensitive material detectors itself, these detectors cannot be densely arranged in some cases.

Japanese Patent Application Laid-Open No. 2001-100432 introduces an exemplary apparatus for processing a photosensitive material provided with detectors for measuring the width of a photosensitive material. However, this apparatus suffers from a different problem that the measured widths contain a considerably high degree of inaccuracy when a photosensitive material deviates from the center of the transport path while being carried.

SUMMARY OF THE INVENTION

The present invention is intended for an apparatus for processing a photosensitive material.

In the apparatus for processing a photosensitive material of the present invention, a photosensitive material is centered with respect to a center of a transport path, and the photosensitive material is processed while traveling along the transport path. The apparatus comprises: a plurality of photosensitive material detectors for detecting the presence or absence of the photosensitive material traveling along the transport path, the plurality of photosensitive material detectors being arranged across the width of the photosensitive material, in an asymmetrical manner with respect to the center of the transport path; and a recognition part for recognizing the width of the photosensitive material based on how many of the plurality of photosensitive material detectors have detected the presence of the photosensitive material.

Thus the width of the printing plate can be measured at increased resolution without densely arranging the plurality of photosensitive material detectors.

Preferably, the recognition part performs certain error recovery, when the photosensitive material is detected by one of the plurality of photosensitive material detectors spaced from the center of the transport path by a first distance while not being detected by another one of the plurality of photosensitive material detectors spaced from the center of the transport path by a second distance smaller than the first distance.

Thus it can be easily judged that the photosensitive has been carried without being centered with respect to the center of the transport path to perform error recovery.

Preferably, the photosensitive material detectors are microswitches detecting the presence of the photosensitive material by contacting the photosensitive material.

Thus the width of the photosensitive material can be easily calculated by a simple configuration.

The present invention is also intended for an area measurement method for measuring the area of a photosensitive material traveling along a predetermined transport path.

It is therefore an object of the present invention to provide an apparatus for processing a photosensitive material and an area measurement method capable of measuring the width of a photosensitive material at high resolution without densely arranging a plurality of photosensitive material detectors. It is another object of the present invention to provide an apparatus for processing a photosensitive material and an area measurement method capable of reducing an error in measured width, even on the occurrence of deviation of a photosensitive material from the center of a transport path.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
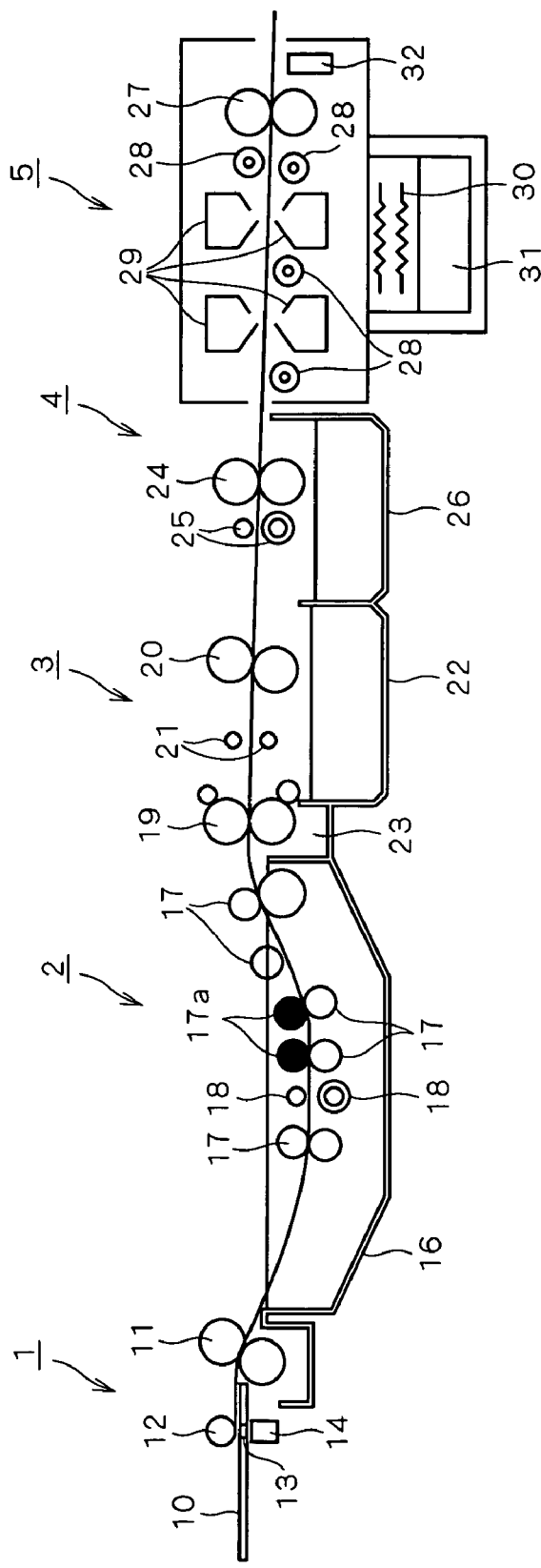
FIG. 1 shows an essential part of an apparatus for processing a printing plate as an apparatus for processing a photosensitive material according to a preferred embodiment of the present invention.
Figure 2:
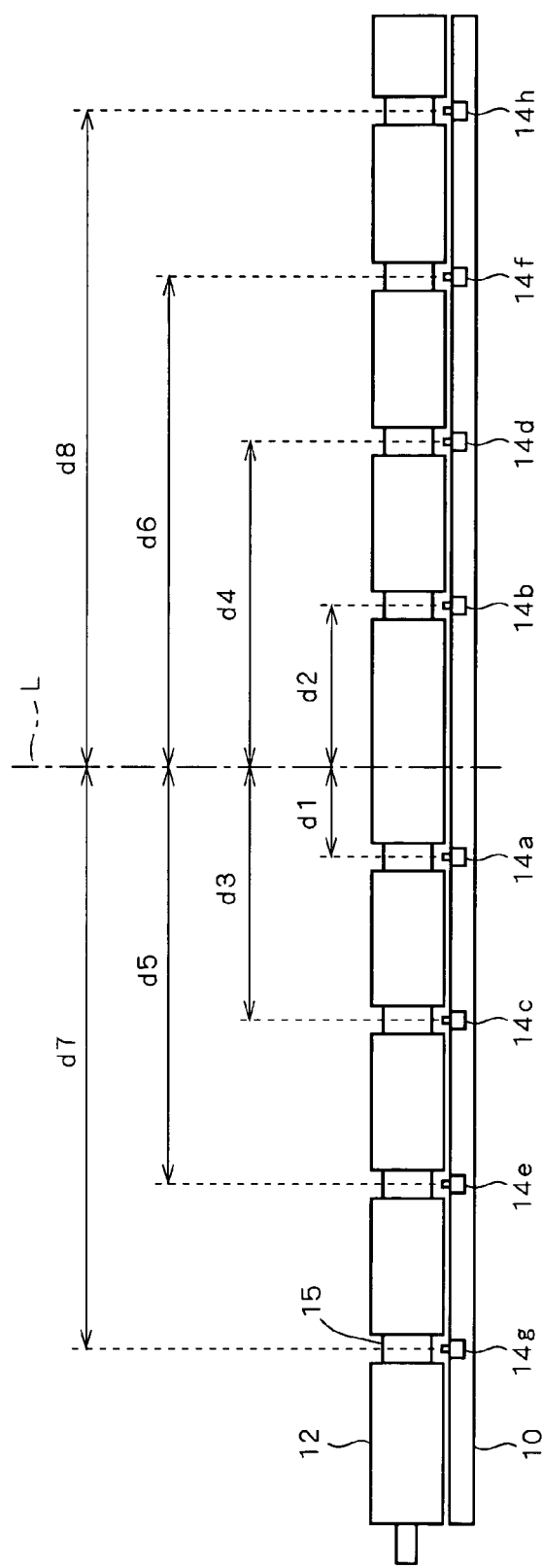
FIG. 2 shows the arrangement of photosensitive material detectors in a receiving section of the apparatus for processing a printing plate.
Figure 3:
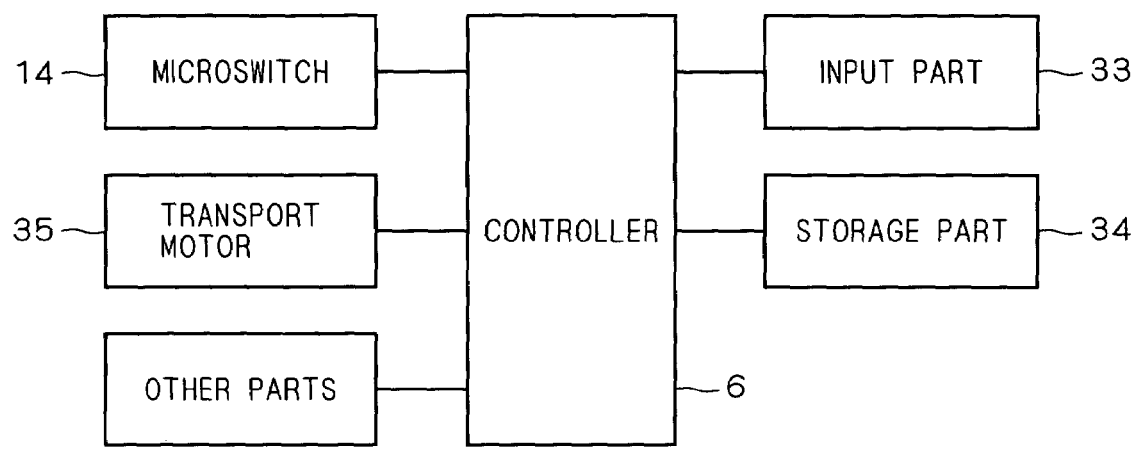
FIG. 3 is a block diagram of the apparatus for processing a printing plate.

The configuration of an apparatus for processing a photosensitive material according to a preferred embodiment of the present invention will be described with reference to FIGS. 1, 2 and 3. FIG. 1 is an exemplary view of an apparatus for processing a printing plate as an apparatus for processing a photosensitive material of the present invention, showing an essential part of the apparatus in a sectional side view. FIG. 2 shows the arrangement of photosensitive material detectors in a receiving section 1 of the apparatus for processing a printing plate when viewed from the front side of the apparatus for processing a printing plate. FIG. 3 is a block diagram of an essential part of the apparatus for processing a printing plate.

With reference to FIG. 1, the apparatus for processing a printing plate of the preferred embodiment of the present invention has a series connection of the receiving section 1 for receiving a printing plate, a development section 2 responsible for development process, a rinsing section 3 responsible for rinsing process, a gum section 4 responsible for gum application, and a drying section 5 responsible for drying process. With reference to FIG. 3, the apparatus for processing a printing plate comprises a controller 6 formed by a microcomputer for controlling each part of the apparatus.

With reference to FIG. 1, the receiving section 1 has a tray 10 for holding thereon a printing plate to be fed into the apparatus, and a pair of feed rollers 11 for feeding the received printing plate to the development section 2 while holding the printing plate therebetween. The receiving section 1 also has a guide roller 12 for guiding the upper surface of the printing plate arranged closer to the entrance than the feed rollers 11. Microswitches 14 are provided below the guide roller 12 such that the microswitches 14 are in contact with a printing plate through holes 13 defined in the tray 10.

With reference to FIG. 2, eight recesses 15 are formed in the guide roller 12. Eight microswitches 14 are provided in one-to-one-correspondence with the recesses 15. The microswitches 14 are arranged such that respective switching actuators enter the corresponding recesses 15. When a printing plate is inserted between the tray 10 and the guide roller 12, the microswitches 14 contacting the printing plate are depressed and then actuated, thereby detecting the presence of the printing plate directly thereabove.

The plurality of microswitches 14 are positioned on both sides with respect to a center line L of the guide roller 12. Microswitches 14a, 14c, 14e and 14g are arranged on the left side, and microswitches 14b, 14d, 14f and 14h are arranged on the right side, in an asymmetrical manner with respect to the center line L in plan view.

More specifically, the microswitches 14a, 14c, 14e and 14g are respectively spaced by distances d1, d3, d5 and d7 from the center line L. The microswitches 14b, 14d, 14f and 14h are respectively spaced by distances d2, d4, d6 and d8 from the center line L. The distances d1, d3, d5 and d7 are respectively different from the distances d2, d4, d6 and d8. The microswitches 14a through 14h are alternately arranged on both sides with respect to the center line L, in the order in which a distance from the center line L increases.

In the apparatus for processing a printing plate of the preferred embodiment of the present invention, a reference line (not shown) is defined in the tray 10 so that the center of the width of a printing plate coincides with the center line L of the guide roller 12.

Accordingly, when a printing plate is inserted into the receiving section 1, the printing plate is detected in different ways. More specifically, the printing plate may be detected only by the microswitch 14a, by the microswitches 14a and 14b, by the microswitches 14a, 14b and 14c, by the microswitches 14a through 14d, by the microswitches 14a through 14e, by the microswitches 14a through 14f, by the microswitches 14a through 14g, or by all of the microswitches 14a through 14h. The width of the printing plate increases in this order. In order for the printing plate to be reliably centered in a transport path, the tray 10 may be provided with a lateral guide member movable along the width of the printing plate.

Again, in the apparatus for processing a printing plate of the preferred embodiment of the present invention, a printing plate is controlled to pass along the center of a transport path, and the plurality of microswitches 14 are arranged in a direction perpendicular to the travel direction of the printing plate (namely, along the width of the printing plate), in an asymmetrical manner with respect to the center line L. Thus the width of the printing plate can be measured at increased resolution without densely arranging the plurality of microswitches 14 on the tray 10.

With reference to the microswitches 14b and 14d adjacent to each other on the right side about the center line L as examples, it will be described how the detection of a printing plate of the preferred embodiment of the present invention differs from the conventional detection. In the conventional arrangement of detectors, when the width of a printing plate of not less than d2×2 and less than d4×2 is to be identified in two stages, another microswitch 14 should be arranged between the microswitches 14b and 14d. However, the microswitches 14 may not be allowed to be arranged densely due to restriction imposed by the size of the microswitches 14 itself. In this case, another microswitch 14 cannot be arranged between the microswitches 14b and 14d.

The preferred embodiment of the present invention employs the mechanical microswitches 14, requiring the recesses 15 in the guide roller 12 at positions facing the microswitches 14. Thus the densely arranged microswitches 14 necessarily require an increasing number of recesses 15, leading to lesser degree of reliability of the guidance of a printing plate by the guide roller 12 and deviation of the printing plate from the center of the transport path. Further, the increase in number of the microswitches 14 is an undesirable in terms of cost effectiveness.

In contrast, in the preferred embodiment of the present invention, the microswitch 14c is arranged on the left side with respect to the center line L by the distance d3 from the center line L. This allows the width of a printing plate of not less than d2×2 and less than d4×2 to be identified in two stages without increasing the density of the microswitches 14 on the right side with respect to the center line L. Thus the number of recesses 15 in the guide roller 12 is not required to be increased so that a printing plate can be guided by the guide roller 12 with a high degree of reliability.

Turning back to FIG. 1, the development section 2 comprises a development tank 16 storing a developer, a plurality of feed rollers 17 arranged in the development tank 16, and a developer discharge part 18 for discharging the developer in the development tank 16. The rollers 17 in the development tank 16 include fuzzy molton rollers 17a contacting the image side of a printing plate. The molton rollers 17a are rotatably driven at a speed different from the speed for driving the other rollers 17 such that a surface of a printing plate is rubbed with the molton rollers 17a. The developer discharge part 18 has spray pipes provided with a plurality of discharge holes (not shown) formed across the width of a printing plate. Using a circulation pump not shown, a developer stored in the development tank 16 is discharged again through the developer discharge part 18 into the development tank 16. The development tank 16 is also provided with a heater not shown intended for temperature control, and a replenishment part not shown for adding a replenisher to the development tank 16.

The rinsing section 3 comprises a pair of squeeze rollers 19 arranged in the former stage for removing a developer from a printing plate carried from the development section 2, a pair of feed rollers 20 arranged in the latter stage, and a rinsing liquid discharge part 21 arranged between the squeeze rollers 19 and the feed rollers 20 and having two spray pipes for discharging a rinsing liquid onto a printing plate. The rinsing section 3 also comprises a rinse tank 22 arranged under the rinsing liquid discharge part 21 for receiving a rinsing liquid flowing down from the rinsing liquid discharge part 21. Using a pump not shown, the rinsing liquid is fed from the rinse tank 22 to the rinsing liquid discharge part 21. An exhaust tank 23 is provided in front of the rinse tank 22 for receiving a developer removed by the squeeze rollers 19.

Likewise, the gum section 4 comprises a pair of feed rollers 24 for carrying a printing plate sent from the rinsing section 3 while holding the printing plate therebetween, a gum liquid discharge part 25 having two spray pipes for discharging a gum liquid onto the printing plate near the feed rollers 24, and a gum liquid tank 26 for receiving a gum liquid flowing down from the gum liquid discharge part 25. The gum section 4 also comprises a pump not shown for feeding a gum liquid stored in the gum liquid tank 26 to the gum liquid discharge part 25.

The drying section 5 comprises a pair of feed rollers 27 for carrying a printing plate while holding the same therebetween, a plurality of tandem rollers 28 for guiding the printing plate, a plurality of air ducts 29 for spraying hot air to the printing plate, and a heater 30 and a blower 31 coupled to the air ducts 29 for producing hot air. A sensor 32 is provided at the exit of the drying section 5 for detecting the ejection of a printing plate.

Next, the configuration including the controller 6 and its surroundings will be discussed with reference to FIG. 3. The controller 6 formed by a microcomputer is connected to an input part 33 allowing a user to actuate the apparatus and create various types of settings, and to a storage part 34 including a ROM storing for example an operation program of the apparatus and a RAM storing user's settings.

In the apparatus for processing a printing plate according to the preferred embodiment of the present invention, each user previously enters predetermined width in one-to-one correspondence with each combination of the microswitches 14 using the input part 33, and stores the input in the storage part 34. That is, the actual width of a printing plate used by each user is stored in correspondence with the range of width defined by each combination of the microswitches 14. Generally, the size and the type of a printing plate are standardized for each user. As an example, the actual size of a printing plate corresponding to full "Kiku" size or half "Kiku" size has only one variation. Then the sizes printing plates to be put in practical use are entered in one-to-one correspondence with the combinations of the microswitches 14, whereby a precise width of a printing plate can be found on the basis of the result of detection by the microswitches 14. In the preferred embodiment of the present invention, a user enters and stores a desirable width of a printing plate in correspondence with each combination of the microswitches 14 to obtain such a precise width. More specifically, the actual sizes of printing plates are entered in correspondence with the detection only by the microswitch 14a, detection by the combination of the microswitches 14a and 14b, detection by the combination of the microswitches 14a, 14b and 14c, detection by the combination of the microswitches 14a through 14d, detection by the combination of the microswitches 14a through 14e, detection by the combination of the microswitches 14a through 14f, detection by the combination of the microswitches 14a through 14g, and detection by the combination of all of the microswitches 14a through 14h.

The sizes of printing plates may not be actually entered. Instead, the respective sizes of various types of printing plates defined by different manufactures are stored in advance in a table memory and a user selects the type of a printing plate to be used, whereby the size of a printing plate can be automatically entered. In this case, a user is allowed to facilitate settings without entering a precise size, thereby causing no typing error in entering a value in correspondence with each microswitch.

The controller 6 is also connected through an input/output part not shown to the microswitches 14 and other parts of the apparatus such as a transport motor 35, whereby the controller 6 is responsible for data entry to each part, control of each part and the like.

The transport motor 35 serves to drive all the rollers 11, 17, 19, 20, 24 and 27 to carry a printing plate. More specifically, the transport motor 35 keeps synchronization between the motors by using a transmission gear not shown to rotatably drive each roller.

Figure 4:
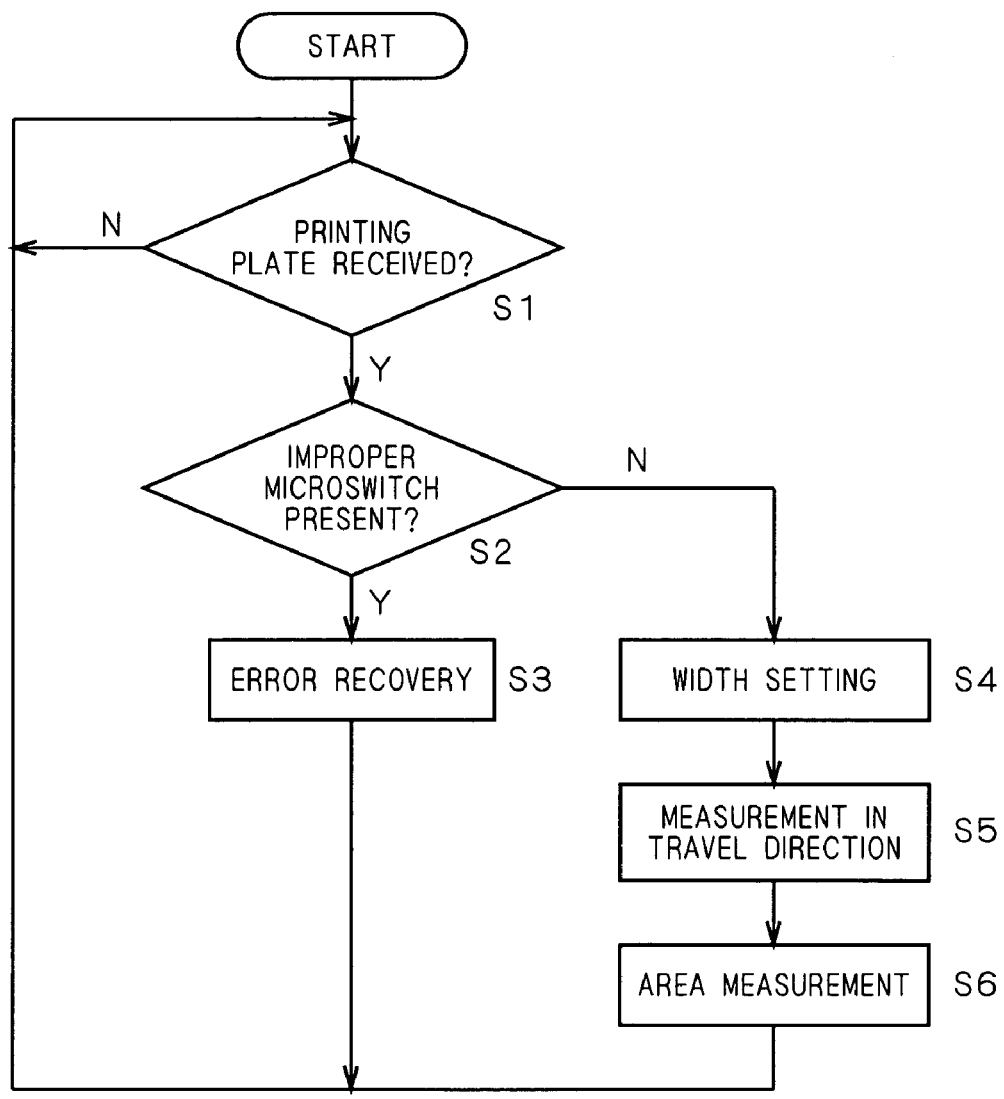
FIG. 4 is a flow chart showing the flow of area calculation steps in the apparatus for processing a printing plate.
Figure 5:
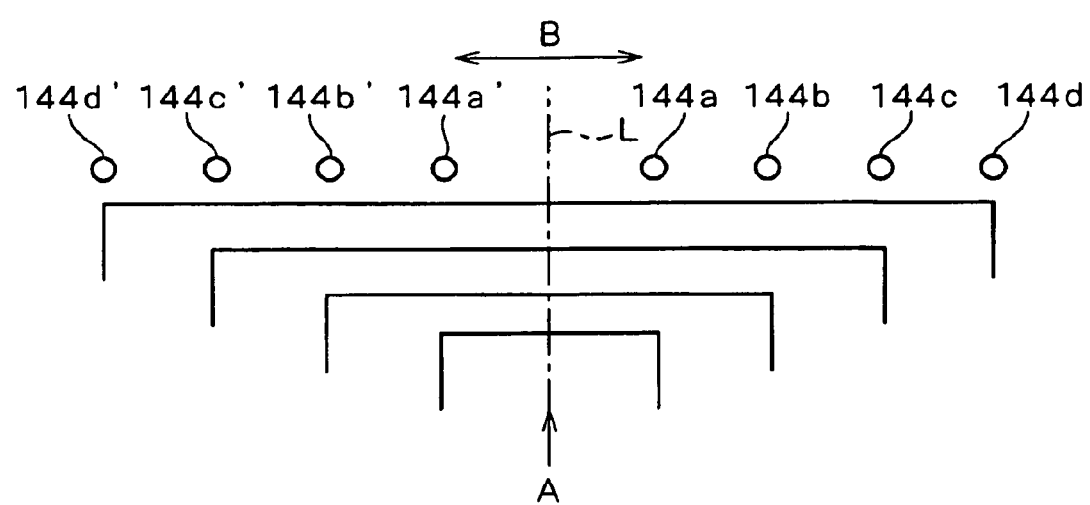
FIG. 5 shows the arrangement of photosensitive material detectors in a conventional apparatus for processing a photosensitive material.

Next, it will be discussed with reference to FIG. 4 how the controller 6 calculates the area of a printing plate in the apparatus for processing a printing plate of the preferred embodiment of the present invention. FIG. 4 is a flow chart showing the flow only of area measurement of a printing plate in this apparatus.

First, with reference to FIG. 4, the microswitch 14 detects the presence of a printing plate to determine whether the printing plate has been received in step S1. If it is judged that the printing plate has been received in step S1, the flow proceeds to step S2.

Next, it is determined whether one or more of the microswitches 14 include an improper microswitch 14 that will be discussed later. When an improper microswitch 14 is present, the flow proceeds to step S3 at which error recovery is performed under the control of the controller 6. As an example, the controller 6 causes an alarm to be activated and urges an operator to insert a printing plate properly centered in the transport path. If a printing plate is reinserted, the flow returns to step S1 to detect the presence of the printing plate.

If there is no improper microswitch 14, the process proceeds to step S4 at which it is decided which combination of the microswitches 14 detected the printing plate to read out the width previously recorded.

The microswitch 14 is deemed to be improper if a printing plate has not been detected by the prescribed combinations discussed above. In the preferred embodiment of the present invention, a printing plate, if inserted while being properly centered, should be detected by the plurality of microswitches 14 in the order in which a distance from the center line L increases. When a printing plate is detected by a first one of the microswitches 14 spaced from the center line L by a first distance while not being detected by a second one of the microswitches 14 spaced from the center line L by a distance smaller than the first distance, it is judged that the printing plate deviates from the center of the transport path. As an example, with reference to FIG. 2, when a printing plate is detected by the microswitch 14b on the right side with respect to the center line L spaced from the center line L by the distance d2 while not being detected by the microswitch 14a on the left side with respect to the center line L spaced from the center line L by the distance d1, it is judged that the printing plate is skewed to the right. The first microswitch 14 (by which the printing plate has been detected while not being detected by the microswitch arranged closer to the center line L than the first microswitch 14) and the second microswitch 14 (by which the printing plate has not been detected while being detected by the microswitch arranged farther from the center line L than the second microswitch 14) are referred to as improper microswitches 14. In this example, the microswitches 14a and 14b are improper microswitches.

Thus in the apparatus for processing a photosensitive material according to the preferred embodiment of the present invention, error recovery is performed on the occurrence of deviation of a printing plate from the center of the transport path and width setting is suspended, thereby generating no error in measured width.

Next, the length of a printing plate in its travel direction is calculated in subsequent step S5. First, a period of time is measured during which the microswitches 14 detect the printing plate. Then the length of the printing plate in its travel direction is calculated based on the measured period of time and a speed of travel of the printing plate obtained from the rotation speed of the transport motor 35.

In subsequent step S6, the area of the printing plate is calculated according to the value obtained in step S5. That is, the area of the printing plate can be precisely calculated from the width and the length in the travel direction of the printing plate. A replenisher is added in a predetermined manner concurrently with this process of measuring area. When the printing plate has passed through the receiving section 1, the flow returns to step S1 to wait for the insertion of another printing plate.

While the invention has been shown and described in detail, the foregoing description is in all aspects illustrative and not restrictive. It is therefore understood that numerous modifications and variations can be devised without departing from the scope of the invention.

What is claimed is:

1. An apparatus for processing a photosensitive material centered with respect to a center of a transport path, in which said photosensitive material is processed while traveling along said transport path, said apparatus comprising:
a plurality of photosensitive material detectors for detecting the presence or absence of said photosensitive material traveling alone said transport path, said plurality of photosensitive material detectors being arranged across the width of said photosensitive material, in an asymmetrical manner with respect to said center of said transport path; and
a recognition part for recognizing the width of said photosensitive material based on how many of said plurality of photosensitive material detectors have detected the presence of said photosensitive material;
wherein said plurality of photosensitive material detectors are alternately arranged on both sides with respect to said center of said transport path, in the order in which a distance from said center of said transport path increases.

2. The apparatus according to claim 1,
wherein said recognition part performs certain error recovery, when said photosensitive material is detected by one of said plurality of photosensitive material detectors spaced from said center of said transport path by a first distance while not being detected by another one of said plurality of photosensitive material detectors spaced from said center of said transport path by a second distance smaller than said first distance.

3. The apparatus according to claim 2,
wherein said photosensitive material detectors are microswitches detecting the presence of said photosensitive material by contacting said photosensitive material.

4. The apparatus according to claim 3, further comprising:
a roller for carrying said photosensitive material along said transport path,
wherein said photosensitive material travels between said roller and said microswitches.

5. The apparatus according to claim 4,
wherein recesses are formed in said roller at positions facing said microswitches.

6. The apparatus according to claim 5, further comprising:
a storage part storing correspondence between the result of detection by said plurality of photosensitive material detectors and the width of said photosensitive material,
wherein said recognition part recognizes the width of said photosensitive material based on said correspondence stored in said storage part.

7. The apparatus according to claim 6, further comprising:
a measuring part for calculating the size of said photosensitive material in a travel direction of said photosensitive material.

8. The apparatus according to claim 7,
wherein said measuring part calculates the size of said photosensitive material in said travel direction of said photosensitive material based on a period of time during which said plurality of photosensitive material detectors detect said photosensitive material and a speed of travel of said photosensitive material.

9. The apparatus according to claim 8, further comprising:
an operation part for calculating the area of said photosensitive material based on the width recognized by said recognition part and the size of said photosensitive material in said travel direction obtained by said measuring part.

10. An area measurement method for measuring the area of a photosensitive material traveling along a predetermined transport path, said method comprising the steps of:
   (a) centering said photosensitive material with respect to a center of said transport path;
   (b) detecting the presence or absence of said photosensitive material at a plurality of points of measurement across the width of said photosensitive material, said plurality of points of measurement being arranged in an asymmetrical manner with respect to said center of said transport path of said photosensitive material;
   (c) recognizing the width of said photosensitive material based on the result of detection obtained in said step (b);
   (d) calculating the size of said photosensitive material in a travel direction of said photosensitive material; and
   (e) calculating the area of said photosensitive material based on the width recognized in said step (c) and the size of said photosensitive material in said travel direction obtained in said step (d),
   wherein said plurality of points of measurement are alternately arranged on both sides with respect to said center of said transport path, in the order in which a distance from said center of said transport path increases.

11. The method according to claim 10,
wherein predetermined error recovery is performed in said step (c), when said photosensitive material is detected at one of said plurality of points of measurement spaced from said center of said transport path by a first distance while not being detected at another one of said plurality of points of measurement spaced from said center of said transport path by a second distance smaller than said first distance.

12. The method according to claim 11, further comprising the step of:
   (f) storing correspondence between the result of detection obtained in said step (b) and the width of said photosensitive material,
   wherein in said step (c), the width of said photosensitive material is recognized based on said correspondence stored in said step (f).

13. The method according to claim 12, wherein in said step (d), the size of said photosensitive material is calculated based on a period of time during which said photosensitive material is detected at said plurality of points of measurement and a speed of travel of said photosensitive material.

* * * * *